United States Patent
Walther et al.

(10) Patent No.: US 10,717,777 B2
(45) Date of Patent: Jul. 21, 2020

(54) SYNTHETIC LUNG SURFACTANT WITH ENHANCED STABILITY AND EFFECTIVENESS

(71) Applicant: The Lundquist Institute for Biomedical Innovation at Harbor-UCLA Medical Center, Torrance, CA (US)

(72) Inventors: Frans J. Walther, Redondo Beach, CA (US); Alan J. Waring, Irvine, CA (US); Larry M. Gordon, Torrance, CA (US)

(73) Assignee: The Lundquist Institute for Biomedical Innovation at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 16/063,437

(22) PCT Filed: Dec. 16, 2016

(86) PCT No.: PCT/US2016/067317
§ 371 (c)(1),
(2) Date: Jun. 18, 2018

(87) PCT Pub. No.: WO2017/106742
PCT Pub. Date: Jun. 22, 2017

(65) Prior Publication Data
US 2019/0085053 A1    Mar. 21, 2019

Related U.S. Application Data

(60) Provisional application No. 62/268,800, filed on Dec. 17, 2015.

(51) Int. Cl.
*C07K 14/785*    (2006.01)
*A61P 11/00*    (2006.01)
*A61K 38/00*    (2006.01)

(52) U.S. Cl.
CPC ............ *C07K 14/785* (2013.01); *A61P 11/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 9,815,869 B2 * | 11/2017 | Notter | C07K 14/47 |
| 2013/0079275 A1 | 3/2013 | Johansson et al. | |
| 2014/0044775 A1 | 2/2014 | Notter et al. | |
| 2015/0125515 A1 * | 5/2015 | Notter | C07K 14/47 |
| | | | 424/450 |

FOREIGN PATENT DOCUMENTS

| | | | | |
|---|---|---|---|---|
| EP | 2644619 A1 * | 10/2013 | ....... | C07K 14/43518 |
| WO | WO 2008/044109 | 4/2008 | | |
| WO | WO 2011/115538 | 9/2011 | | |

OTHER PUBLICATIONS

International Search Report and Written Opinion of PCT/US2016/067317 dated Apr. 13, 2017 (9 pages).

* cited by examiner

*Primary Examiner* — Christina Bradley
(74) *Attorney, Agent, or Firm* — Sheppard Mullin Richter & Hampton LLP

(57) ABSTRACT

Peptides suitable for preparation of lung surfactants are described. Examples include one that include a first fragment comprising the amino acid sequence of XWLXRALIKRIQAZI (SEQ ID NO: 1) or a first amino acid sequence having at least 90% sequence identity to SEQ ID NO: 1 and a second fragment comprising the amino acid sequence of RZLPQLVXRLVLRXS (SEQ ID NO: 2) or a second amino acid sequence having at least 90% sequence identity to SEQ ID NO: 2, wherein X is any amino acid but at least one amino acid at the X positions is not cysteine, or Z is any amino acid but at least one amino acid at the Z positions is not methionine. Surfactants that contain such peptides, and related compositions, methods of preparing and using the compositions are also described.

20 Claims, 4 Drawing Sheets
Specification includes a Sequence Listing.

SEQUENCE LISTING

```
<160> NUMBER OF SEQ ID NOS: 59

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<223> OTHER INFORMATION: See specification as filed for detailed
      description of substitutions and preferred embodiments

<400> SEQUENCE: 1

Xaa Trp Leu Xaa Arg Ala Leu Ile Lys Arg Ile Gln Ala Xaa Ile
1               5                   10                  15

<210> SEQ ID NO 2
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<223> OTHER INFORMATION: See specification as filed for detailed
      description of substitutions and preferred embodiments

<400> SEQUENCE: 2

Arg Xaa Leu Pro Gln Leu Val Xaa Arg Leu Val Leu Arg Xaa Ser
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Lys Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ala Thr Lys
1

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Pro Ile Pro Leu Pro Tyr
1               5

<210> SEQ ID NO 6
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser
65                  70                  75

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Phe Pro Ile Pro Leu Pro Tyr Cys Trp Leu Cys Arg Ala Leu Ile Lys
1               5                   10                  15

Arg Ile Gln Ala Met Ile Pro Lys Gly Gly Arg Met Leu Pro Gln Leu
            20                  25                  30

Val Cys Arg Leu Val Leu Arg Cys Ser
        35                  40

<210> SEQ ID NO 8
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Phe Pro Ile Pro Leu Pro Tyr Cys Trp Leu Cys Arg Ala Leu Ile Lys
1               5                   10                  15

Arg Ile Gln Ala Met Ile Asp Ala Thr Lys Arg Met Leu Pro Gln Leu
            20                  25                  30

Val Cys Arg Leu Val Leu Arg Cys Ser
        35                  40

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Cys Trp Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser

<210> SEQ ID NO 10
<211> LENGTH: 34
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 10

Cys Trp Leu Cys Arg Ala Leu Ile Lys Arg Ile Gln Ala Met Ile Asp
1               5                   10                  15

Ala Thr Lys Arg Met Leu Pro Gln Leu Val Cys Arg Leu Val Leu Arg
            20                  25                  30

Cys Ser

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Trp Leu Tyr Arg Ala Leu Ile Lys Arg Ile Gln Ala Leu Ile
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Trp Leu Tyr Arg Ala Leu Ile Lys Arg Ile Gln Ala Leu Ile
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Trp Leu Tyr Arg Ala Leu Ile Lys Arg Ile Gln Ala Leu Ile
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Trp Leu Tyr Arg Ala Leu Ile Lys Arg Ile Gln Ala Leu Ile
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Tyr Trp Leu Phe Arg Ala Leu Ile Lys Arg Ile Gln Ala Leu Ile
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Trp Leu Phe Arg Ala Leu Ile Lys Arg Ile Gln Ala Leu Ile
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Trp Leu Phe Arg Ala Leu Ile Lys Arg Ile Gln Ala Leu Ile
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Trp Leu Phe Arg Ala Leu Ile Lys Arg Ile Gln Ala Leu Ile
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Leu Leu Pro Gln Leu Val Tyr Arg Leu Val Leu Arg Tyr Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Leu Leu Pro Gln Leu Val Tyr Arg Leu Val Leu Arg Leu Ser
1               5                   10                  15

<210> SEQ ID NO 21
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 21

Arg Leu Leu Pro Gln Leu Val Tyr Arg Leu Val Leu Arg Ala Ser
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Leu Leu Pro Gln Leu Val Tyr Arg Leu Val Leu Arg Phe Ser
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Leu Leu Pro Gln Leu Val Phe Arg Leu Val Leu Arg Tyr Ser
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Leu Leu Pro Gln Leu Val Phe Arg Leu Val Leu Arg Leu Ser
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Leu Leu Pro Gln Leu Val Phe Arg Leu Val Leu Arg Ala Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Leu Leu Pro Gln Leu Val Phe Arg Leu Val Leu Arg Phe Ser
1               5                   10                  15
```

<210> SEQ ID NO 27
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Phe Pro Ile Pro Leu Pro Tyr Tyr Trp Leu Tyr Arg Ala Leu Ile Lys
1               5                   10                  15

Arg Ile Gln Ala Leu Ile Pro Lys Gly Gly Arg Leu Leu Pro Gln Leu
            20                  25                  30

Val Tyr Arg Leu Val Leu Arg Tyr Ser
        35                  40

<210> SEQ ID NO 28
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Phe Pro Ile Pro Leu Pro Tyr Leu Trp Leu Tyr Arg Ala Leu Ile Lys
1               5                   10                  15

Arg Ile Gln Ala Leu Ile Pro Lys Gly Gly Arg Leu Leu Pro Gln Leu
            20                  25                  30

Val Tyr Arg Leu Val Leu Arg Leu Ser
        35                  40

<210> SEQ ID NO 29
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Phe Pro Ile Pro Leu Pro Tyr Ala Trp Leu Tyr Arg Ala Leu Ile Lys
1               5                   10                  15

Arg Ile Gln Ala Leu Ile Pro Lys Gly Gly Arg Leu Leu Pro Gln Leu
            20                  25                  30

Val Tyr Arg Leu Val Leu Arg Ala Ser
        35                  40

<210> SEQ ID NO 30
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Phe Pro Ile Pro Leu Pro Tyr Phe Trp Leu Phe Arg Ala Leu Ile Lys
1               5                   10                  15

Arg Ile Gln Ala Leu Ile Pro Lys Gly Gly Arg Leu Leu Pro Gln Leu
            20                  25                  30

Val Phe Arg Leu Val Leu Arg Phe Ser 35                  40

<210> SEQ ID NO 31
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Phe Pro Ile Pro Leu Pro Tyr Leu Trp Leu Phe Arg Ala Leu Ile Lys
1               5                   10                  15

Arg Ile Gln Ala Leu Ile Pro Lys Gly Gly Arg Leu Leu Pro Gln Leu
            20                  25                  30

Val Phe Arg Leu Val Leu Arg Leu Ser
            35                  40

<210> SEQ ID NO 32
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Phe Pro Ile Pro Leu Pro Tyr Ala Trp Leu Phe Arg Ala Leu Ile Lys
1               5                   10                  15

Arg Ile Gln Ala Leu Ile Pro Lys Gly Gly Arg Leu Leu Pro Gln Leu
            20                  25                  30

Val Phe Arg Leu Val Leu Arg Ala Ser
            35                  40

<210> SEQ ID NO 33
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Phe Pro Ile Pro Leu Pro Tyr Tyr Trp Leu Phe Arg Ala Leu Ile Lys
1               5                   10                  15

Arg Ile Gln Ala Leu Ile Pro Lys Gly Gly Arg Leu Leu Pro Gln Leu
            20                  25                  30

Val Phe Arg Leu Val Leu Arg Tyr Ser
            35                  40

<210> SEQ ID NO 34
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Phe Pro Ile Pro Leu Pro Tyr Phe Trp Leu Tyr Arg Ala Leu Ile Lys
1               5                   10                  15

Arg Ile Gln Ala Leu Ile Pro Lys Gly Gly Arg Leu Leu Pro Gln Leu
            20                  25                  30

Val Tyr Arg Leu Val Leu Arg Phe Ser
        35                  40

<210> SEQ ID NO 35
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Phe Pro Ile Pro Leu Pro Tyr Tyr Trp Leu Tyr Arg Ala Leu Ile Lys
1               5                   10                  15

Arg Ile Gln Ala Leu Ile Asp Ala Thr Lys Arg Leu Leu Pro Gln Leu
            20                  25                  30

Val Tyr Arg Leu Val Leu Arg Tyr Ser
        35                  40

<210> SEQ ID NO 36
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Phe Pro Ile Pro Leu Pro Tyr Leu Trp Leu Tyr Arg Ala Leu Ile Lys
1               5                   10                  15

Arg Ile Gln Ala Leu Ile Asp Ala Thr Lys Arg Leu Leu Pro Gln Leu
            20                  25                  30

Val Tyr Arg Leu Val Leu Arg Leu Ser
        35                  40

<210> SEQ ID NO 37
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Phe Pro Ile Pro Leu Pro Tyr Ala Trp Leu Tyr Arg Ala Leu Ile Lys
1               5                   10                  15

Arg Ile Gln Ala Leu Ile Asp Ala Thr Lys Arg Leu Leu Pro Gln Leu
            20                  25                  30

Val Tyr Arg Leu Val Leu Arg Ala Ser
        35                  40

<210> SEQ ID NO 38
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Phe Pro Ile Pro Leu Pro Tyr Phe Trp Leu Phe Arg Ala Leu Ile Lys
1               5                   10                  15

Arg Ile Gln Ala Leu Ile Asp Ala Thr Lys Arg Leu Leu Pro Gln Leu
            20                  25                  30

Val Phe Arg Leu Val Leu Arg Phe Ser
        35                  40

<210> SEQ ID NO 39
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Phe Pro Ile Pro Leu Pro Tyr Leu Trp Leu Phe Arg Ala Leu Ile Lys
1               5                   10                  15

Arg Ile Gln Ala Leu Ile Asp Ala Thr Lys Arg Leu Leu Pro Gln Leu
            20                  25                  30

Val Phe Arg Leu Val Leu Arg Leu Ser
        35                  40

<210> SEQ ID NO 40
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Phe Pro Ile Pro Leu Pro Tyr Ala Trp Leu Phe Arg Ala Leu Ile Lys
1               5                   10                  15

Arg Ile Gln Ala Leu Ile Asp Ala Thr Lys Arg Leu Leu Pro Gln Leu
            20                  25                  30

Val Phe Arg Leu Val Leu Arg Ala Ser
        35                  40

<210> SEQ ID NO 41
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Phe Pro Ile Pro Leu Pro Tyr Tyr Trp Leu Phe Arg Ala Leu Ile Lys
1               5                   10                  15

Arg Ile Gln Ala Leu Ile Asp Ala Thr Lys Arg Leu Leu Pro Gln Leu
            20                  25                  30

Val Phe Arg Leu Val Leu Arg Tyr Ser
        35                  40

<210> SEQ ID NO 42
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Phe Pro Ile Pro Leu Pro Tyr Phe Trp Leu Tyr Arg Ala Leu Ile Lys
1               5                   10                  15

Arg Ile Gln Ala Leu Ile Asp Ala Thr Lys Arg Leu Leu Pro Gln Leu

```
                    20                  25                  30

Val Tyr Arg Leu Val Leu Arg Phe Ser
        35                  40

<210> SEQ ID NO 43
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Tyr Trp Leu Tyr Arg Ala Leu Ile Lys Arg Ile Gln Ala Leu Ile Pro
1               5                   10                  15

Lys Gly Gly Arg Leu Leu Pro Gln Leu Val Tyr Arg Leu Val Leu Arg
            20                  25                  30

Tyr Ser

<210> SEQ ID NO 44
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Leu Trp Leu Tyr Arg Ala Leu Ile Lys Arg Ile Gln Ala Leu Ile Pro
1               5                   10                  15

Lys Gly Gly Arg Leu Leu Pro Gln Leu Val Tyr Arg Leu Val Leu Arg
            20                  25                  30

Leu Ser

<210> SEQ ID NO 45
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Trp Leu Tyr Arg Ala Leu Ile Lys Arg Ile Gln Ala Leu Ile Pro
1               5                   10                  15

Lys Gly Gly Arg Leu Leu Pro Gln Leu Val Tyr Arg Leu Val Leu Arg
            20                  25                  30

Ala Ser

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Phe Trp Leu Phe Arg Ala Leu Ile Lys Arg Ile Gln Ala Leu Ile Pro
1               5                   10                  15

Lys Gly Gly Arg Leu Leu Pro Gln Leu Val Phe Arg Leu Val Leu Arg
            20                  25                  30
```

Phe Ser

```
<210> SEQ ID NO 47
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47
```

Leu Trp Leu Phe Arg Ala Leu Ile Lys Arg Ile Gln Ala Leu Ile Pro
1               5                   10                  15

Lys Gly Gly Arg Leu Leu Pro Gln Leu Val Phe Arg Leu Val Leu Arg
            20                  25                  30

Leu Ser

```
<210> SEQ ID NO 48
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

Ala Trp Leu Phe Arg Ala Leu Ile Lys Arg Ile Gln Ala Leu Ile Pro
1               5                   10                  15

Lys Gly Gly Arg Leu Leu Pro Gln Leu Val Phe Arg Leu Val Leu Arg
            20                  25                  30

Ala Ser

```
<210> SEQ ID NO 49
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49
```

Tyr Trp Leu Phe Arg Ala Leu Ile Lys Arg Ile Gln Ala Leu Ile Pro
1               5                   10                  15

Lys Gly Gly Arg Leu Leu Pro Gln Leu Val Phe Arg Leu Val Leu Arg
            20                  25                  30

Tyr Ser

```
<210> SEQ ID NO 50
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

Phe Trp Leu Tyr Arg Ala Leu Ile Lys Arg Ile Gln Ala Leu Ile Pro
1               5                   10                  15

Lys Gly Gly Arg Leu Leu Pro Gln Leu Val Tyr Arg Leu Val Leu Arg
            20                  25                  30

Phe Ser

<210> SEQ ID NO 51
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Tyr Trp Leu Tyr Arg Ala Leu Ile Lys Arg Ile Gln Ala Leu Ile Asp
1               5                   10                  15

Ala Thr Lys Arg Leu Leu Pro Gln Leu Val Tyr Arg Leu Val Leu Arg
            20                  25                  30

Tyr Ser

<210> SEQ ID NO 52
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Leu Trp Leu Tyr Arg Ala Leu Ile Lys Arg Ile Gln Ala Leu Ile Asp
1               5                   10                  15

Ala Thr Lys Arg Leu Leu Pro Gln Leu Val Tyr Arg Leu Val Leu Arg
            20                  25                  30

Leu Ser

<210> SEQ ID NO 53
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Trp Leu Tyr Arg Ala Leu Ile Lys Arg Ile Gln Ala Leu Ile Asp
1               5                   10                  15

Ala Thr Lys Arg Leu Leu Pro Gln Leu Val Tyr Arg Leu Val Leu Arg
            20                  25                  30

Ala Ser

<210> SEQ ID NO 54
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Phe Trp Leu Phe Arg Ala Leu Ile Lys Arg Ile Gln Ala Leu Ile Asp
1               5                   10                  15

Ala Thr Lys Arg Leu Leu Pro Gln Leu Val Phe Arg Leu Val Leu Arg
            20                  25                  30

Phe Ser

<210> SEQ ID NO 55
<211> LENGTH: 34
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 55

Leu Trp Leu Phe Arg Ala Leu Ile Lys Arg Ile Gln Ala Leu Ile Asp
1               5                   10                  15

Ala Thr Lys Arg Leu Leu Pro Gln Leu Val Phe Arg Leu Val Leu Arg
            20                  25                  30

Leu Ser

<210> SEQ ID NO 56
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Trp Leu Phe Arg Ala Leu Ile Lys Arg Ile Gln Ala Leu Ile Asp
1               5                   10                  15

Ala Thr Lys Arg Leu Leu Pro Gln Leu Val Phe Arg Leu Val Leu Arg
            20                  25                  30

Ala Ser

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Tyr Trp Leu Phe Arg Ala Leu Ile Lys Arg Ile Gln Ala Leu Ile Asp
1               5                   10                  15

Ala Thr Lys Arg Leu Leu Pro Gln Leu Val Phe Arg Leu Val Leu Arg
            20                  25                  30

Tyr Ser

<210> SEQ ID NO 58
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Phe Trp Leu Tyr Arg Ala Leu Ile Lys Arg Ile Gln Ala Leu Ile Asp
1               5                   10                  15

Ala Thr Lys Arg Leu Leu Pro Gln Leu Val Tyr Arg Leu Val Leu Arg
            20                  25                  30

Phe Ser

<210> SEQ ID NO 59
<211> LENGTH: 41
<212> TYPE: PRT
<213> ORGANISM: Artificial Sequence
<220> FEATURE:
<223> OTHER INFORMATION: Description of Artificial Sequence: Synthetic
```

```
    polypeptide

<400> SEQUENCE: 59

Phe Pro Ile Pro Leu Pro Tyr Cys Trp Leu Cys Arg Ala Leu Ile Lys
1               5                   10                  15

Arg Ile Gln Ala Met Ile Asp Ala Thr Lys Arg Met Leu Pro Gln Leu
            20                  25                  30

Val Cys Arg Leu Val Leu Arg Cys Ser
        35                  40
```

SYNTHETIC LUNG SURFACTANT WITH ENHANCED STABILITY AND EFFECTIVENESS

CROSS REFERENCE TO RELATED APPLICATIONS

This application is a national stage of International Application No. PCT/US2016/067317 filed Dec. 16, 2016, which claims benefit under 35 U.S.C. § 119(e) to U.S. Provisional Application Ser. No. 62/268,800, filed Dec. 17, 2015, the entire disclosure of which is hereby incorporated by reference.

GOVERNMENT LICENSE RIGHTS

This invention was made with government support under R01HL092158 and R01ES015330 awarded by the National Institute of Health. The government has certain rights in the invention.

SEQUENCE LISTING

The instant application contains a Sequence Listing which has been filed electronically in ASCII format and is hereby incorporated by reference in its entirety. Said ASCII copy, created on Nov. 15, 2018, is named 0WVR-225782-US_S-L.txt and is 24,967 bytes in size.

BACKGROUND

When endogenous lung surfactant is deficient or becomes dysfunctional in humans, it can be replaced by exogenous surface-active substitutes. Therapy with active exogenous surfactant drugs has proven to be life-saving in preventing and treating the neonatal respiratory distress syndrome (NRDS) in preterm infants, and on-going research is studying the feasibility of efficaciously extending surfactant therapy to pediatric and adult patients with clinical acute lung injury (ALI) or acute respiratory distress syndrome (ARDS). Developing effective surfactant therapy for ALI-IARDS is particularly challenging, and requires the use of exogenous surfactants having maximal surface and pulmonary activity, plus the ability to resist inhibition from endogenous substances present in injured lungs as a result of permeability edema or in association with the inflammatory response.

Synthetic lung surfactants have a number of important advantages over current animal-derived surfactants as pharmaceutical products for treating NRDS and ALI/ARDS. In research on synthetic surfactant development, particular emphasis has been placed on designing peptide mimics of natural surfactant proteins, but more research is needed to identify peptides that are highly effective, stable, and easy to manufacture.

SUMMARY

The present disclosure provides peptides suitable for preparation of surfactants. Surfactants that contain such peptides, and related compositions, methods of preparing and using the compositions are also described. In one embodiment, the peptide includes an N-terminal helix, connected optionally through a turn, to a C-terminal helix of the alpha helix of surfactant protein (SP)-B. The N-terminal or C-terminal helix can be modified, as compared to the natural SP-B peptide, with one or more substitutions at the cysteine and/or methionine residues. In some embodiments, the turn is a natural or designer loop peptide sequence that facilitates formation of a helix-turn-helix structure.

Table A below lists the amino acid sequences, SEQ ID NOs and, in some cases, short names for various peptides disclosed in the present application.

TABLE A

| Peptide Sequences and Names | |
|---|---|
| SEQ ID NO: 1 | XWLXRALIKRIQAZI |
| SEQ ID NO: 2 | RZLPQLVXRLVLRXS |
| SEQ ID NO: 3 | PKGG |
| SEQ ID NO: 4 | DATK |
| SEQ ID NO: 5 | FPIPLPY |
| SEQ ID NO: 11 | YWLYRALIKRIQALI |
| SEQ ID NO: 12 | LWLYRALIKRIQALI |
| SEQ ID NO: 13 | AWLYRALIKRIQALI |
| SEQ ID NO: 14 | FWLYRALIKRIQALI |
| SEQ ID NO: 15 | YWLFRALIKRIQALI |
| SEQ ID NO: 16 | LWLFRALIKRIQALI |
| SEQ ID NO: 17 | AWLFRALIKRIQALI |
| SEQ ID NO: 18 | FWLFRALIKRIQALI |
| SEQ ID NO: 19 | RLLPQLVYRLVLRYS |
| SEQ ID NO: 20 | RLLPQLVYRLVLRLS |
| SEQ ID NO: 21 | RLLPQLVYRLVLRAS |

TABLE A-continued

Peptide Sequences and Names

| SEQ ID NO: 22 | RLLPQLVYRLVLRFS |
| --- | --- |
| SEQ ID NO: 23 | RLLPQLVFRLVLRYS |
| SEQ ID NO: 24 | RLLPQLVFRLVLRLS |
| SEQ ID NO: 25 | RLLPQLVFRLVLRAS |
| SEQ ID NO: 26 | RLLPQLVFRLVLRFS |

Alpha-helix of SP-B:
FPIPLPYCWLCRALIKRIQAMIPKGALAVAVAQVCRVVPLVAGGICQCLAERYSVILLDTLLGRMLPQ
LVCRLVLRCS (SEQ ID NO: 6)

```
Super Mini-B:   FPIPLPYCWLCRALIKRIQAMIPKGGRMLPQLVCRLVLRCS  (SEQ ID NO: 7)
B-YL:           FPIPLPYYWLYRALIKRIQALIPKGGRLLPQLVYRLVLRYS  (SEQ ID NO: 27)
B-LYL:          FPIPLPYLWLYRALIKRIQALIPKGGRLLPQLVYRLVLRLS  (SEQ ID NO: 28)
B-AYL:          FPIPLPYAWLYRALIKRIQALIPKGGRLLPQLVYRLVLRAS  (SEQ ID NO: 29)
B-FFL:          FPIPLPYFWLFRALIKRIQALIPKGGRLLPQLVFRLVLRFS  (SEQ ID NO: 30)
B-LFL:          FPIPLPYLWLFRALIKRIQALIPKGGRLLPQLVFRLVLRLS  (SEQ ID NO: 31)
B-AFL:          FPIPLPYAWLFRALIKRIQALIPKGGRLLPQLVFRLVLRAS  (SEQ ID NO: 32)
B-YFL:          FPIPLPYYWLFRALIKRIQALIPKGGRLLPQLVFRLVLRYS  (SEQ ID NO: 33)
B-FYL:          FPIPLPYFWLYRALIKRIQALIPKGGRLLPQLVYRLVLRFS  (SEQ ID NO: 34)

SMB-DATK:       FPIPLPYCWLCRALIKRIQAMIDATKRMLPQLVCRLVLRCS  (SEQ ID NO: 8)
B-DATK-YL:      FPIPLPYYWLYRALIKRIQALIDATKRLLPQLVYRLVLRYS  (SEQ ID NO: 35)
B-DATK-LYL:     FPIPLPYLWLYRALIKRIQALIDATKRLLPQLVYRLVLRLS  (SEQ ID NO: 36)
B-DATK-AYL:     FPIPLPYAWLYRALIKRIQALIDATKRLLPQLVYRLVLRAS  (SEQ ID NO: 37)
B-DATK-FFL:     FPIPLPYFWLFRALIKRIQALIDATKRLLPQLVFRLVLRFS  (SEQ ID NO: 38)
B-DATK-LFL:     FPIPLPYLWLFRALIKRIQALIDATKRLLPQLVFRLVLRLS  (SEQ ID NO: 39)
B-DATK-AFL:     FPIPLPYAWLFRALIKRIQALIDATKRLLPQLVFRLVLRAS  (SEQ ID NO: 40)
B-DATK-YFL:     FPIPLPYYWLFRALIKRIQALIDATKRLLPQLVFRLVLRYS  (SEQ ID NO: 41)
B-DATK-FYL:     FPIPLPYFWLYRALIKRIQALIDATKRLLPQLVYRLVLRFS  (SEQ ID NO: 42)

Mini-B:         CWLCRALIKRIQAMIPKGGRMLPQLVCRLVLRCS         (SEQ ID NO: 9)
MB-YL:          YWLYRALIKRIQALIPKGGRLLPQLVYRLVLRYS         (SEQ ID NO: 43)
MB-LYL:         LWLYRALIKRIQALIPKGGRLLPQLVYRLVLRLS         (SEQ ID NO: 44)
MB-AYL:         AWLYRALIKRIQALIPKGGRLLPQLVYRLVLRAS         (SEQ ID NO: 45)
ME-FEL:         FWLFRALIKRIQALIPKGGRLLPQLVFRLVLRFS         (SEQ ID NO: 46)
MB-LFL:         LWLFRALIKRIQALIPKGGRLLPQLVFRLVLRLS         (SEQ ID NO: 47)
MB-AFL:         AWLFRALIKRIQALIPKGGRLLPQLVFRLVLRAS         (SEQ ID NO: 48)
MB-YFL:         YWLFRALIKRIQALIPKGGRLLPQLVFRLW,RYS         (SEQ ID NO: 49)
MB-FYL:         FWLYRALIKRIQALIPKGGRLLPQLVYRLVLRFS         (SEQ ID NO: 50)

MB-DATK:        CWLCRALIKRIQAMIDATKRMLPQLVCRLVLRCS         (SEQ ID NO: 10)
MB-DATK-YL:     YWLYRALIKRIQALIDATKRLLPQLVYRLVLRYS         (SEQ ID NO: 51)
MB-DATK-LYL:    LWLYRALIKRIQALIDATKRLLPQLVYRLVLRLS         (SEQ ID NO: 52)
MB-DATK-AYL:    AWLYRALIKRIQALIDATKRLLPQLVYRLVLRAS         (SEQ ID NO: 53)
MB-DATK-FFL:    FWLFRALIKRIQALIDATKRLLPQLVFRLVLRFS         (SEQ ID NO: 54)
MB-DATK-LFL:    LWLFRALIKRIQALIDATKRLLPQLVFRLVLRLS         (SEQ ID NO: 55)
MB-DATK-AFL:    AWLFRALIKRIQALIDATKRLLPQLVFRLVLRAS         (SEQ ID NO: 56)
MB-DATK-YFL:    YWLFRALIKRIQALIDATKRLLPQLVFRLVLRYS         (SEQ ID NO: 57)
MB-DATK-FYL:    FWLYRALIKRIQALIDATKRLLPQLVYRLVLRFS         (SEQ ID NO: 58)

S-MM DATK:      FPIPLPYCWLCRALIKRIQAMIDATKRMLPQLVCRLVLRCS  (SEQ ID NO: 59)
```

In one embodiment, provided is an isolated peptide comprising (i) a first fragment comprising the amino acid sequence of XWLXRALIKRIQAZI (SEQ ID NO: 1) or a first amino acid sequence having at least 90% sequence identity to SEQ ID NO: 1 and (ii) a second fragment comprising the amino acid sequence of RZLPQLVXRLV-LRXS (SEQ ID NO: 2) or a second amino acid sequence having at least 90% sequence identity to SEQ ID NO: 2, wherein: (a) X is any amino acid but at least one amino acid at the X positions is not cysteine, or (b) Z is any amino acid but at least one amino acid at the Z positions is not methionine.

In some aspects, the peptide further comprises (iii) a turn between the first fragment and the second fragment. In some aspects, the turn comprises PKGG (SEQ ID NO: 3). In some aspects, the turn can form a salt bridge between amino acids within the turn or between the turn and the first or second fragment. In some aspects, the turn comprises DATK (SEQ ID NO: 4).

In some aspects, the first fragment is at the N-terminal end of the second fragment. In some aspects, the peptide further comprises an insertion sequence at the N-terminal end of the first fragment. In some aspects, the insertion sequence comprises FPIPLPY (SEQ ID NO: 5).

In some aspects, the peptide is 100 amino acids in length or shorter. In some aspects, the peptide is 80 amino acids in length or shorter.

In some aspects, at least one amino acid at the X positions is not cysteine. In some aspects, each amino acid at the X positions is not cysteine. In some aspects, the amino acid at each X position is selected from the group consisting of Y, L, A, and F.

In some aspects, at least one amino acid at the Z positions is not methionine. In some aspects, each amino acid at the Z position is not methionine. In some aspects, the amino acid at each X position is leucine.

In some aspects, the first fragment comprises any amino acid sequence of SEQ ID NO: 11-18, an amino acid sequence having at least 90% sequence identity to any amino acid sequence of SEQ ID NO: 11-18, or an amino acid sequence derived from any amino acid sequence of SEQ ID NO: 11-18 with one, two or three amino acid addition, deletion and/or substitution.

In some aspects, the second fragment comprises any amino acid sequence of SEQ ID NO: 19-26, an amino acid sequence having at least 90% sequence identity to any amino acid sequence of SEQ ID NO: 19-26, or an amino acid sequence derived from any amino acid sequence of SEQ ID NO: 19-26 with one, two or three amino acid addition, deletion and/or substitution.

In some aspects, the peptide comprises any amino acid sequence of SEQ ID NO: 27-58, an amino acid sequence having at least 90% sequence identity to any amino acid sequence of SEQ ID NO: 27-58, or an amino acid sequence derived from any amino acid sequence of SEQ ID NO: 27-58 with one, two or three amino acid addition, deletion and/or substitution.

Also provided, in one embodiment, is a composition comprising a peptide of the present disclosure and one or more phospholipid. In some aspects, the one or more phospholipid is selected from the group consisting of dipalmitoylphosphatidylcholine (DPPC), palmitoyloleoylphosphatidylcholine (POPC), phosphatidylglycerol (PG), palmitoyloleoylphosphatidylglycerol (POPG), cholesterol (Chol), 1,2-Dioleoyl-sn-glycero-3-phosphocholine (DOPC), 1-Palmitoyl-2-oleoyl-sn-glycero-3-phosphoethanolamine (POPE), 1-palmitoyl-2-oleoylsn-glycero phosphocholine (POPS), 1,2-Distearoyl-sn-glycero-3-phosphocholine (DSPC), 1,2-Dipalmitoyl-sn-glycero-3-phosphoethanolamine (DPPE), 1,2-dipalmitoyl-sn-glycero-3-phosphoglycerol (DPPG), a diether phosphonolipid analog of DPPC (DEPN-8), C16:0, C16:1 diether phosphonoglycerol (PG-1) and combinations thereof.

In some aspects, the one or more phospholipid comprises DPPC, POPC and POPG. In some aspects, the DPPC, POPC and POPG are at ratio of about (4-6):(2-4):(1-3).

Also provided, in one embodiment, is a method of treating surfactant deficiency or dysfunction in a patient in need thereof, comprising administration to the patient a composition of the present disclosure. In some aspects, the surfactant deficiency or dysfunction comprises a respiratory distress syndrome in an infant or a respiratory distress syndrome secondary to surfactant deficiency or lung immaturity in a premature or near-term infant.

DETAILED DESCRIPTION

Figure 1:
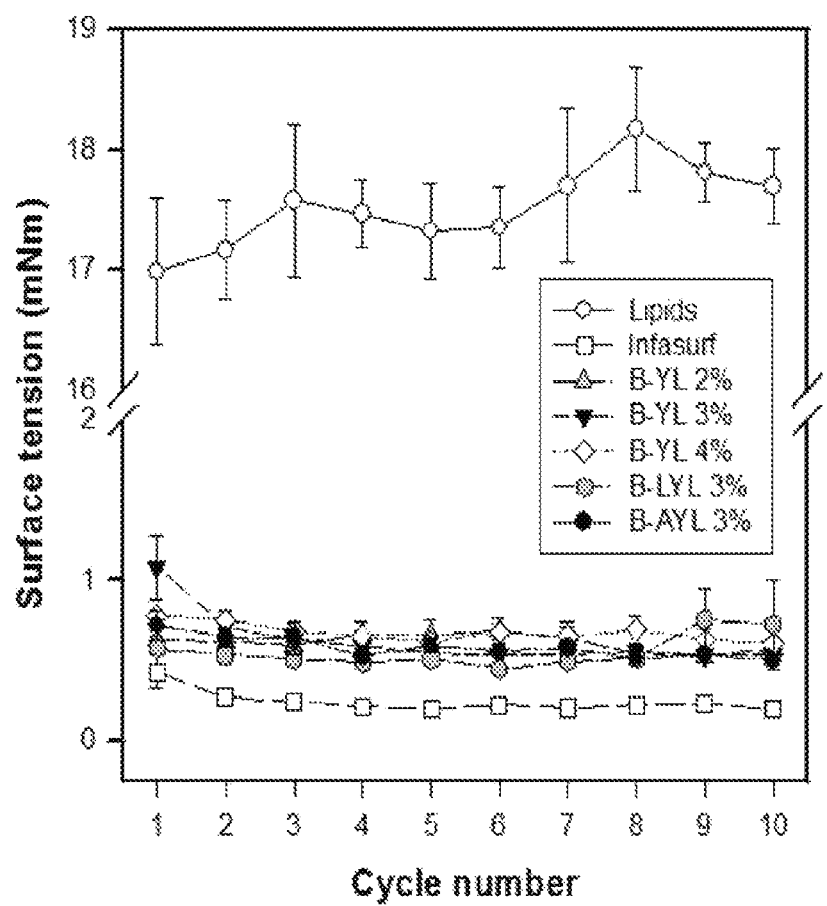
FIG. 1 shows surface activity (low surface tension equals high surface activity) measured with captive bubble surfactometry of 2, 3 and 4% of B-YL peptide (SEQ ID NO: 27), 3% of B-LYL peptide (SEQ ID NO: 28) and 3% of B-AYL peptide (SEQ ID NO: 29) in DPPC:POPC:POPG 5:3:2 (wt:wt:wt) in comparison with the clinical bovine surfactant Infasurf (positive control) and lipids only (negative control). Minimum tension values during the first 10 cycles of quasi-static cycling on the captive bubble surfactometer are depicted and show excellent surface activity (as shown by surface tension values <<2 mNm) for Infasurf, the 3 concentrations of B-YL peptide and the B-LYL and B-AYL peptides in lipids versus poor surface activity of lipids only.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a peptide" includes a plurality of peptides.

1. Definitions

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "sequence identity" refers to a level of amino acid residue or nucleotide identity between two peptides or between two nucleic acid molecules. When a position in the compared sequence is occupied by the same base or amino acid, then the molecules are identical at that position. A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure.

Likewise, the present disclosure also includes sequences that have one, two, three, four, or five substitution, deletion or addition of amino acid residues or nucleotides as compared to the reference sequences.

In any of the embodiments described herein, analogs of a peptide comprising any amino acid sequence described herein are also provided, which have at least about 80%, or at least about 83%, or at least about 85%, or at least about 90%, or at least about 95%, or at least about 98%, or at least about 99% sequence identity to any of reference amino acid sequences. In some embodiments, the analogs include one, two, three, four, or five substitution, deletion or addition of amino acid residues as compared to the reference sequences. In some embodiments, the substitution is a conservative substitution.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in Table B.

TABLE B

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S—Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | (a) Val, D-Val, Met, D-Met, D-Ile, D-Leu, Ile |
| Lysine | D-Lys, Arg, D-Arg, Orn, D-Orn |

TABLE B-continued

| For Amino Acid | Replace With |
| --- | --- |
| Methionine | (b) D-Met, S—Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | (c) D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier. In certain embodiments, the composition is formulated as a film, gel, patch, or liquid solution.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the internal surface of the lung.

2. Surfactant Peptides

In one embodiment, the present disclosure provides peptides suitable for preparation of surfactants. In one embodiment, the peptide includes an N-terminal helix, connected optionally through a turn, to a C-terminal helix of the alpha helix of surfactant protein (SP)-B. The N-terminal or C-terminal helix can be modified, as compared to the natural SP-B peptide, with one or more substitutions at the cysteine and/or methionine residues. In some embodiments, the turn is a natural or designer loop peptide sequence that facilitates formation of a helix-turn-helix structure.

The sequence of the alpha-helix of SP-B is provided in Table A (SEQ ID NO: 6), where the N-terminal helix and the C-terminal helix are underlined. Two example peptides that include these helices are also listed in Table A, short-named "Mini-B or MB" (SEQ ID NO: 9) and "Super Mini-B or SMB" (SEQ ID NO: 7). In addition to the helices, Mini-B further includes a "PKGG" turn (SEQ ID NO: 3). Super Mini-B then further includes the "insertion sequence" (SEQ ID NO: 5) from the natural SP-B peptide.

The Mini-B and Super Mini-B peptides can be modified by replacing the PKGG turn (SEQ ID NO: 3) with another turn, such as DATK (SEQ ID NO: 4) which is discovered to be able to increase molecular stability and improve the ease of synthesis, folding and purification of the peptides. Example analogs in this respect include SMB-DATK (SEQ ID NO: 8) and MB-DATK (SEQ ID NO: 10).

In some embodiments, any of these amino acid sequences can further be modified within either or both the helix regions. In one embodiment, at least one, two, three, or four, or all of the cysteines in the helix is substituted with another amino acid. In one embodiment, at least one cysteine in each helix is substituted wither another amino acid. In one embodiment, at least one of the helices has no cysteine residue. In one embodiment, the entire peptide includes no cysteine. In some embodiments, the substitution is with Y, L, A, or F.

Surprisingly, it is discovered that, even when the cysteines are substituted resulting in removal of the disulfide bonds, the peptide can still form a desired helix-turn-helix structure and is more stable and effective. In some examples, when the cysteines are substituted with one or more tyrosine residues, the hydrophobic core formed by the tyrosine residues can further help stabilize the peptide.

In one embodiment, at least one of the methionine residues is substituted with another amino acid. In one embodiment, both of the methionine residues are substituted. In some embodiments, the substitution is with leucine. Also surprisingly, such a substitution does not change the structure of the peptide but rather makes it more stable and easier to fold and manufacture. Further, the removal of methionine renders the peptide resisting oxidative stress.

In one embodiment, provided is an isolated peptide comprising (i) a first fragment comprising the amino acid sequence of XWLXRALIKRIQAZI (SEQ ID NO: 1) or a first amino acid sequence having at least 90% (or at least 80%, 85% or 95%) sequence identity to, or alternatively having 1, 2, or 3 addition, deletion and/or substation from, SEQ ID NO: 1 and (ii) a second fragment comprising the amino acid sequence of RZLPQLVXRLVLRXS (SEQ ID NO: 2) or a second amino acid sequence having at least 90% (or at least 80%, 85% or 95%) sequence identity to, or alternatively having 1, 2, or 3 addition, deletion and/or substation from SEQ ID NO: 2, wherein: (a) X is any amino acid but at least one amino acid at the X positions is not cysteine, or (b) Z is any amino acid but at least one amino acid at the Z positions is not methionine.

Non-limiting examples of SEQ ID NO: 1 include SEQ ID NO: 11-18. Non-limiting examples of SEQ ID NO: 2 include SEQ ID NO: 19-26.

In some embodiments, the peptide further includes a turn between the first fragment and the second fragment. A "turn" as used herein, refers to a relatively short (e.g., less than 50 amino acids in length) amino acid fragment that forms a secondary structure in a polypeptide chain where the polypeptide chain reverses its overall direction. Examples of turns include, without limitation, α-turns, β-turns, γ-turns, δ-turns, π-turns, loops, multiple turns and hairpins. The turn is typically from one amino acid to about 50 amino acids (or to about 45, 40, 35, 30, 25, 20, 15, 10, 9, 8, 7, 6 or 5 amino acids) in length. In some embodiment, the turn does not include cysteine. In some embodiments, the turn does not include methionine.

In some embodiments, the turn includes an amino acid that forms a salt bridge with either of the helices. In some embodiments, the turn includes amino acids to form a salt bridge within.

Non-limiting examples of turns include PKGG (SEQ ID NO: 3), DATK (SEQ ID NO: 4) and amino acids 23-63 of SEQ ID NO: 6 or a portion or combination of portions thereof.

It is contemplated that the helices can be orientated either way. In one embodiment, SEQ ID NO: 1 (or the first fragment) can be at the N-terminal direction of SEQ ID NO: 2 (or the second fragment). In one embodiment, SEQ ID NO: 1 (or the first fragment) can be at the C-terminal direction of SEQ ID NO: 2 (or the second fragment).

In some embodiments, the peptide further includes an insertion sequence at the N-terminal end of the peptide. In some embodiments, the peptide further includes an insertion sequence at the N-terminal direction of the first fragment or the N-terminal direction of the second fragment. The insertion sequence, in some embodiments, includes at least one proline. In another embodiment, the insertion sequence includes at least a leucine or isoleucine. A non-limiting example of the insertion sequence is FPIPLPY (SEQ ID NO: 5).

The total length of the peptide varies from 20 amino acids to about 100 amino acids. In one embodiment, the peptide is not longer than about 100, or 90, 80, 70, 60 or 50 amino acids long.

Non-limiting examples of the peptides include SEQ ID NO: 27-58 or an amino acid sequence having at least 90% (or at least 80%, 85% or 95%) sequence identity to any amino acid sequence of SEQ ID NO: 27-58, or an amino acid sequence derived from any amino acid sequence of SEQ ID NO: 27-58 with one, two or three amino acid addition, deletion and/or substitution.

3. Synthesis of Surfactant Peptides

The peptides described herein can be ordered from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification. Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled biochemist.

The peptides can be also prepared by using recombinant expression systems. Generally, this involves inserting the nucleic acid molecule into an expression system to which the molecule is heterologous (i.e., not normally present). One or more desired nucleic acid molecules encoding a peptide of the disclosure may be inserted into the vector. When multiple nucleic acid molecules are inserted, the multiple nucleic acid molecules may encode the same or different peptides. The heterologous nucleic acid molecule is inserted into the expression system or vector in proper sense (5→3') orientation relative to the promoter and any other 5' regulatory molecules, and correct reading frame.

The nucleic acid molecules can be derived from the known SP-B nucleotides. In certain embodiments, it may be desirable to prepare codon-enhanced nucleic acids that will favor expression of the desired peptide in the transgenic expression system of choice.

The preparation of the nucleic acid constructs can be carried out using methods well known in the art. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture. Other vectors are also suitable.

Once a suitable expression vector is selected, the desired nucleic acid sequences are cloned into the vector using standard cloning procedures in the art. The vector is then introduced to a suitable host.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Alternatively, if the peptide of interest is not secreted, it can be isolated from the recombinant cells using standard isolation and purification schemes. This includes disrupting the cells (e.g., by sonication, freezing, French press, etc.) and then recovering the peptide from the cellular debris. Purification can be achieved using the centrifugation, precipitation, and purification procedures described above.

Whether the peptide of interest is secreted or not, it may also contain a purification tag (such as poly-histidine, a glutathione-5-transferase, or maltose-binding protein (MBP-)), which assists in the purification but can later be removed, i.e., cleaved from the peptide following recovery. Protease-specific cleavage sites can be introduced between the purification tag and the desired peptide. The desired peptide product can be purified further to remove the cleaved purification tags.

4. Surfactant Compositions and Formulations

Surfactants and compositions that include any one or more of the peptides as disclosed herein are also provided. In one embodiment, the composition includes any one or more of the peptides and one or more phospholipid.

There are an abundance of kinds of phospholipids suitable for use in surfactants. Non-limiting examples include dipalmitoylphosphatidylcholine (DPPC), palmitoyloleoyl-phosphatidylcholine (POPC), phosphatidylglycerol (PG), palmitoyloleoylphosphatidylglycerol (POPG), cholesterol (Chol), glycerophospholipids such as 1,2-Dioleoyl-sn-glycero-3-phosphocholine (DOPC), 1-Palmitoyl-2-oleoyl-sn-glycero-3-phosphoethanolamine (POPE), 1-palmitoyl-2-oleoylsn-glycero phosphocholine (POPS), 1,2-Distearoyl-sn-glycero-3-phosphocholine (DSPC), 1,2-Dipalmitoyl-sn-glycero-3-phosphoethanolamine (DPPE), 1,2-dipalmitoyl-sn-glycero-3-phosphoglycerol (DPPG) and diether phosphonolipid analogs of DPPC and phosphatidylglycerol (e.g., DEPN-8 and PG-1).

The phospholipids can be mixed at suitable ratios, in some embodiments. For instance, DPPC:POPC:POPG can be used a ratio of about 5:3:2, DPPC:POPG at a ratio of about 7:3, DEPN-8:PG-1 at about 9:1 or 8:2. In a particular example, the phospholipids include DPPC, POPC and POPG. In one aspect, the DPPC, POPC and POPG are at ratio of about (4-6):(2-4):(1-3).

In various embodiments described herein, the peptides described herein can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Non-conservative substitutions may too be possible, provided that they do not substantially affect the binding activity of the peptide (i.e., collagen binding affinity).

The surfactant compositions can further include any one or more of a non-phospho surfactant. As used herein, the term "non-phospho surfactant" refers to surface active compounds that do not possess a phospho group (e.g., phosphate, phosphonate, etc.). Exemplary non-phospho surfactants include, without limitation, a free fatty acid, hexadecanol, or cholesterol.

Preferred free fatty acids include saturated and monounsaturated $C_{10}$ to $C_{24}$ hydrocarbons, more preferably $C_{12}$-$C_{20}$ hydrocarbons, most preferably $C_{14}$-$C_{18}$ hydrocarbons. Of these, saturated hydrocarbons are preferred.

The peptides or compositions of the present disclosure can be used for delivering pharmaceutical agents to a subject in need thereof. In one embodiment, the composition (or formulation) includes a peptide or composition of the earlier disclosure and a therapeutic agent. The therapeutic agent can be any agent that is shown, tested, or proposed to have therapeutic effects.

5. Methods

The surfactant compositions of the present disclosure can be used to treat lung tissue that is characterized by deficiency and/or dysfunction of endogenous surfactant (i.e., "surfactant deficient or dysfunctional lung tissue"). In certain embodiments, the deficiency of endogenous surfactant can be a reduced amount or an abnormal composition of endogenous surfactant (i.e., not enough is present or the composition thereof is ineffective) or the complete absence of an endogenous surfactant, and the surfactant dysfunction can be a reduced activity of endogenous surfactant either present intrinsically or acquired during disease. Thus, the term "treatment" of surfactant deficient and/or dysfunctional lung tissue is meant to include a prophylactic or therapeutic regimen that can inhibit onset of RDS, for example, in premature infants, or the onset of acute lung injury (ALI) or the acute respiratory distress syndrome (ARDS) in patients of any age, or otherwise improve respiratory function, lung pressure-volume mechanics, or clinical outcome when administered for therapeutic treatment of a pre-existing conditions such as acute or neonatal RDS, or ALI, or ARDS. As used herein, "treatment" contemplates complete therapeutic resolution of a condition as well as improving conditions to minimize symptoms of RDS or ALI/ARDS.

The treatments in accordance with this aspect of the disclosure involve administering a surfactant composition of the present disclosure to a patient having lung tissue characterized by endogenous surfactant deficiency and/or dysfunction, where the administering is carried out under conditions effective to coat alveolar surfaces of the affected lung tissue with the surfactant composition, thereby treating the surfactant deficient and/or dysfunctional lung tissue.

The patient to be treated can be a premature infant who is characterized by either the complete absence of endogenous surfactant or an ineffective amount of endogenous surfactant or an acquired dysfunction of endogenous surfactant during the clinical course. In either case, the surfactant composition of the present disclosure can be administered in a manner effective to prevent onset of neonatal respiratory distress syndrome (when administered immediately following intubation), or reduce the severity of respiratory deficit in acute respiratory distress syndrome and/or acute lung injury (when administered some time after initial intubation). Administration of the surfactant composition is preferably via aspiration, airway instillation, aerosolization, or nebulization. Administration of the surfactant can be administered periodically over a course of treatment to maintain lung function in the infant, preferably until the infant's lung tissue is capable of producing sufficient endogenous surfactant to maintain lung function in the absence of intervention.

The patient to be treated can also be an individual that otherwise should be able to produce active endogenous surfactant, but due to lung tissue disease or disorder either has deficient levels of endogenous surfactant or existing endogenous surfactant has become inhibited or inactivated in activity. In this embodiment, the patient is a full-term infant, child, or adult. Endogenous surfactant production can be deficient due to acute lung injury caused by pulmonary disease or infection, systemic disease or infection, or other direct or indirect causes such as burns, trauma, shock, aspiration syndromes, drug overdose, multiple blood transfusions, pancreatitis, or other known causes of ALI/ARDS. In either acquired surfactant deficiency or dysfunction, the surfactant composition of the present disclosure can be administered in a manner effective to reduce the severity of respiratory deficit in acute respiratory distress syndrome and/or acute lung injury. The surfactant composition may also be administered prophylactically to such patients to prevent the onset of ALI/ARDS. Administration of the surfactant composition is preferably via aspiration, airway instillation, aerosolization, or nebulization. Administration of the surfactant can be administered periodically over a course of treatment to maintain lung function in the individual being treated.

Another aspect of the present disclosure relates to a method of delivering a therapeutic agent (examples provided above). By virtue of the surface activity of the compositions of the present disclosure, it is believed that the surfactant compositions of the present disclosure will readily form liposomal vesicles that can be used to deliver therapeutic agents to a patient. Thus, this method of the present disclosure includes introducing a therapeutic agent into a surfactant composition of the present disclosure under conditions effective to encapsulate the therapeutic agent in liposomal vesicles, and then administering the composition to a subject under conditions effective to deliver the therapeutic agent to a target tissue. The administration can be any suitable approach for delivery of the therapeutic agent to a target tissue, but preferably aspiration, airway instillation, aerosolization, nebulization, intranasal instillation, oral or oropharyngeal instillation, intraperitoneal injection, or intravascular injection. The target tissue can be lung tissue or a systemic tissue. The agent or agents to be delivered can be any pharmaceutical or therapeutic agent including those listed above as well as a systemic or local anti-tumor agent, a systemic or local gene therapy agent, a systemic or local anti-inflammatory agent or antioxidant, a systemic or local vasoactive agent, a systemic or local agent modifying immune responses, blood cells, or host-defense.

Devices useful for administering the surfactants are also disclosed, such as for nasal, oropharyngeal or intratracheal delivery. For instance, US 2014/0216449 describes devices for surfactant administration and ventilation of low birth weight infants.

EXAMPLES

Example 1

In Vitro Testing of Surface Activity

In this example, surface activity of the various peptides disclosed in the present disclosure were measured in mixtures of peptides and lipids using captive bubble surfactometry.

This example used peptide concentrations of 2-4% and a lipid mixture consisting of 5:3:2 (wt:wt:wt) DPPC:POPC:POPG. Lipids only were used a negative control and the clinical surfactant Infasurf™ as a positive control. Sequences of B-YL, B-LYL, B-LYL and B-AYL are shown in Table 1.

FIG. 1 shows surface activity measured with captive bubble surfactometry of three concentrations of B-YL peptide (SEQ ID NO: 27; 2, 3 and 4%), 3% of B-LYL petide (SEQ ID NO: 28) and 3% of B-AYL peptide (SEQ ID NO: 29) in DPPC:POPC:POPG 5:3:2 (wt:wt:wt) in comparison with the clinical bovine surfactant Infasurf (positive control) and lipids only (negative control). Low surface tension equals high surface activity.

Minimum tension values during the first 10 cycles of quasi-static cycling on the captive bubble surfactometer are compared with those of lipids only. The results show excellent surface activity (as shown by low surface tension values) for Infasurf, the three concentrations of B-YL peptide in lipids, 3% of B-LYL, and 3% of B-AYL (mean values <<2 mN/m), but poor surface activity of lipids only.

Figure 2:
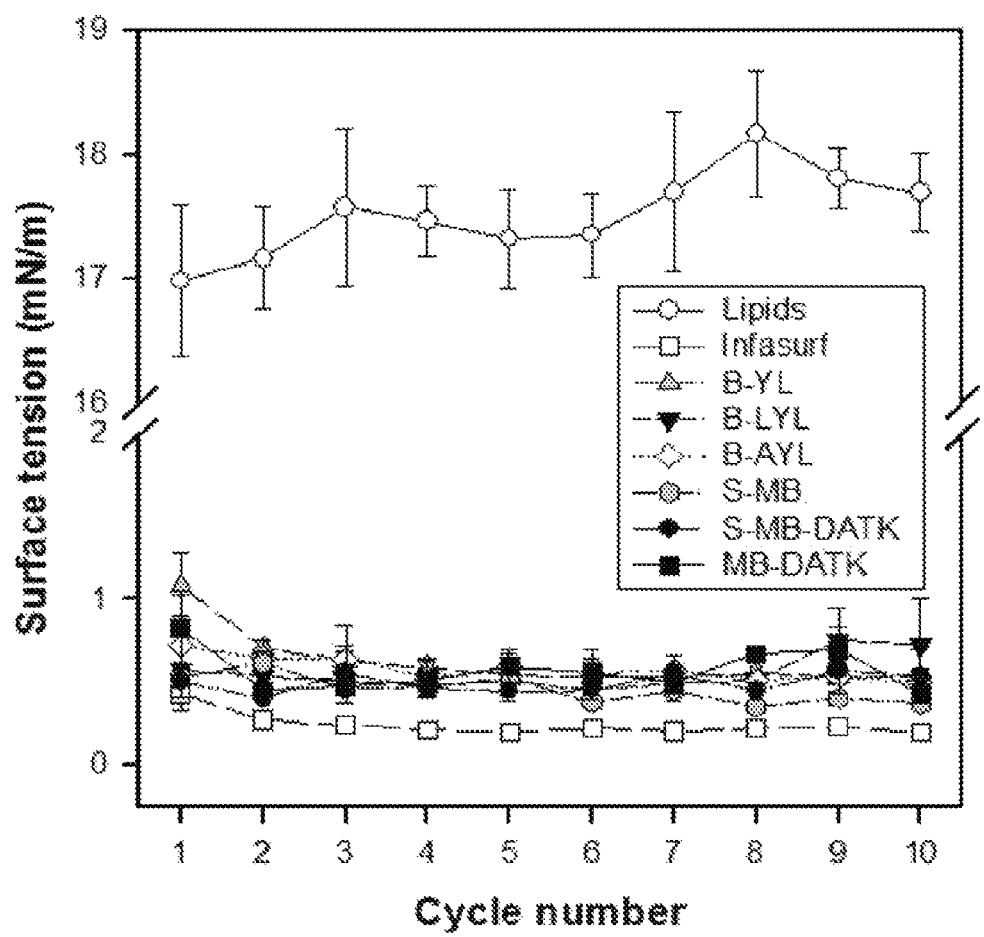
FIG. 2 compares 3% of B-YL (SEQ ID NO: 27), B-LYL (SEQ ID NO: 28) and B-AYL (SEQ ID NO: 29) in 5:3:2 (wt:wt:wt) DPPC:POPC:POPG with lipids only (negative control) and the clinical surfactant Infasurf™ (positive control). Surface activity of Super Mini-B (S-MB), Super Mini-B-DATK (S-MB-DATK) and Mini-B-DATK (MB-DATK) has been added for comparison.

FIG. 2 compares 3% of B-YL (SEQ ID NO: 27), B-LYL (SEQ ID NO: 28) and B-AYL (SEQ ID NO: 29) in 5:3:2 (wt:wt:wt) DPPC:POPC:POPG with lipids only (negative control) and the clinical surfactant Infasurf™ (positive control). For comparison the minimum surface tension values of Super Mini-B (S-MB), Super Mini-B-DATK (S-MB-DATK) and Mini-B-DATK (MB-DATK) have been added to the figure. Likewise, the results show excellent surface activity of these surfactant peptides as compared to the negative control.

Example 2

Computer Modeling of B-YL Peptide

The three-dimensional (3D) structure of the B-YL peptide (SEQ ID NO: 27) was predicted using the I-TASSER service (see zhanglab.ccmb.med.umich.edu/I-TASSER), which uses a homology algorithm based on multiple PDB (Protein Data Bank) depositions to model distinct regions of the protein. I-TASSER is an automated pipeline for structure predictions using multiple threading alignments and simulations of iterative assemblies, and has successfully predicted a range of protein structures. The B-YL primary sequence was submitted to I-TASSER V4.3, and three distinct models were obtained. Model 1 with the highest C-score was selected, and its accuracy was estimated from the following parameters: C-score of −0.57, TM-score of 0.64±0.13 and RMSD of 3.3±2.3 Å. C-score is a confidence score for evaluating the quality of I-TASSER models (between −5 to 2), with elevated values indicating a model with high confidence. TM-score is a scale for quantifying the similarity between two structures, with scores greater than 0.50 signifying a model of correct topology and scores less than 0.17 implying random similarity. Last, RMSD (i.e., root mean square deviation) is an average distance of all residue pairs in two structures. The high C- and TM-scores, together with the low RMSD, indicate that Model 1 provides accurate estimates of the secondary and tertiary structures for the B-YL mimic.

Figure 3:
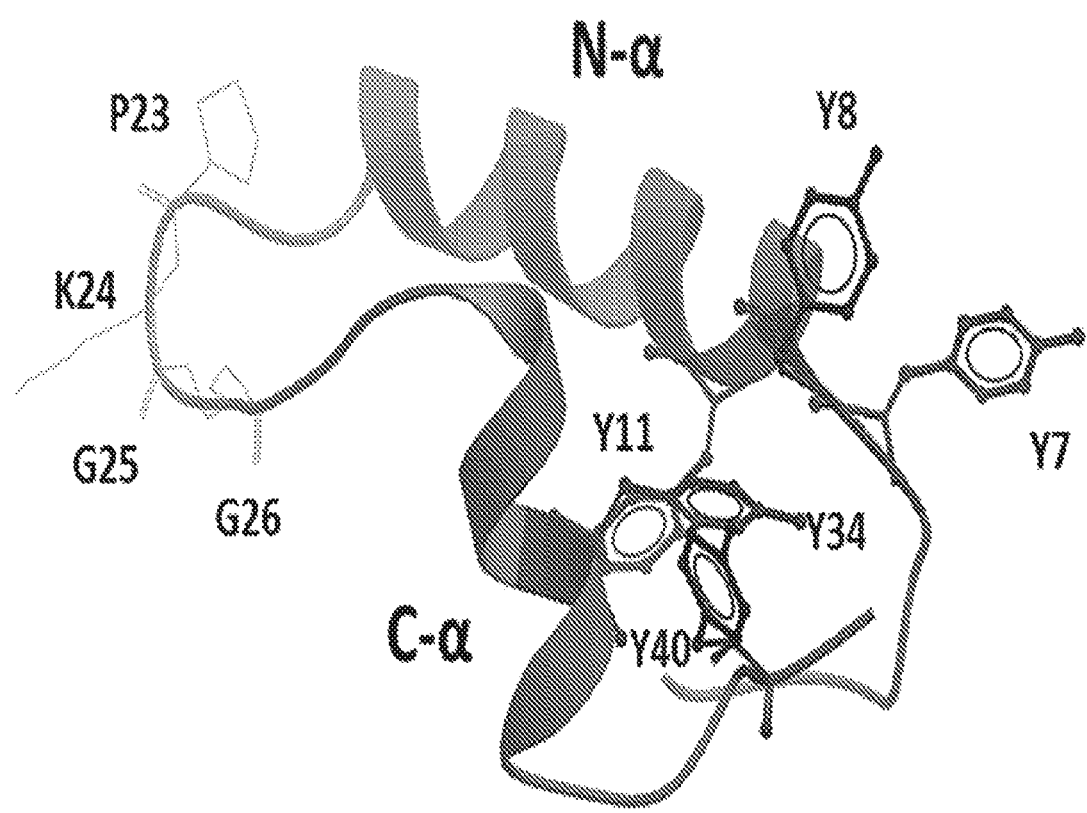
FIG. 3 shows a Molsoft representation of the I-TASSER Model 1 for the B-YL mimic. The predicted 3D-structure indicates that the B-YL primary sequence (SEQ ID NO: 27) folds with an N-terminal α-helix (residues 7-21; background) connected to a C-terminal α-helix (30-37; foreground) via a turn (P23-G26). The parent (Y7) and substituted (Y8, Y11, Y34 and Y40) tyrosines are shown as stick figures, and are clustered to the right.

A Molsoft representation of the I-TASSER Model 1 for the B-YL peptide was generated. The predicted 3D-structure, as shown in FIG. 3, indicates that the B-YL primary sequence folds with an N-terminal α-helix (residues 7-21; background) connected to a C-terminal α-helix (30-37; foreground) via a turn (P23-G26). The parent (Y7) and substituted (Y8, Y11, Y34 and Y40) tyrosines are shown as stick figures, and are clustered to the right.

In this context, note that Model 1 of the B-YL mimic adopts an α-helix—turn—α-helix motif that is similar to those reported for the oxidized forms of the parent Mini-B and Super Mini-B peptides. With the oxidized Mini-B and Super Mini-B peptides, however, disulfide cross-linkages (e.g., Cys-8 to Cys-40 and Cys-11 to Cys-34 in Super Mini-B) were inserted to strengthen the helix—turn—helix conformation of the respective peptides. Extensive functional studies indicated that high surfactant activities were only observed for Mini-B and Super Mini-B peptides that assumed a compact helix-turn-helix structure.

Unlike the disulfide bonds that reinforce the helix—turn—helix of oxidized Mini-B and Super Mini-B, however, the corresponding α-helix—turn of B-YL in FIG. 3 may be stabilized by a strong hydrophobic core formed by clustered Tyr residues (e.g., Y11, Y34 and Y40) that replace the parents' Cys residues. The driving force behind this Tyr clustering may be due to "π-stacking" interactions of aromatic groups in close proximity. Consequently, the high in vitro surfactant activities seen for B-YL (FIGS. 1 and 2) suggest that non-covalent hydrophobic interactions between clustered Tyr residues (FIG. 3) is an effective replacement for covalent-linked disulfides. Additional named sequences in this application with Tyr and Phe residues at various positions can similarly have elevated surfactant activities via this proposed mechanism.

Further, the relative membrane affinities of the B-YL peptides and other named sequences were studied using Membrane Protein Explorer (MPEx; Version 3.2.9). MPEx is a Java program that analyses hydrophobic lipid-protein interactions in membranes (blanco.biomol.uci.ed/mpex). With the hydropathy analysis mode, hydropathy plots were produced using the augmented Wimley-White (WW) whole-residue hydrophobicity scale that predicts membrane-associated helices with high accuracy. Peptide sequences were submitted to MPEx, and the resulting plots are presented as hydropathy (kcal/mol) versus the sequence residue number, averaged over a sliding window of 19 amino-acid residues. Higher positive hydropathy values reflect enhanced lipid bilayer partitioning for any putative membrane helices. Hydrophobic amino-acid substitutions (e.g., Leu or Phe) will raise the hydropathy, while polar amino-acid replacements (Arg or Lys) will lower the hydropathy.

Figure 4:
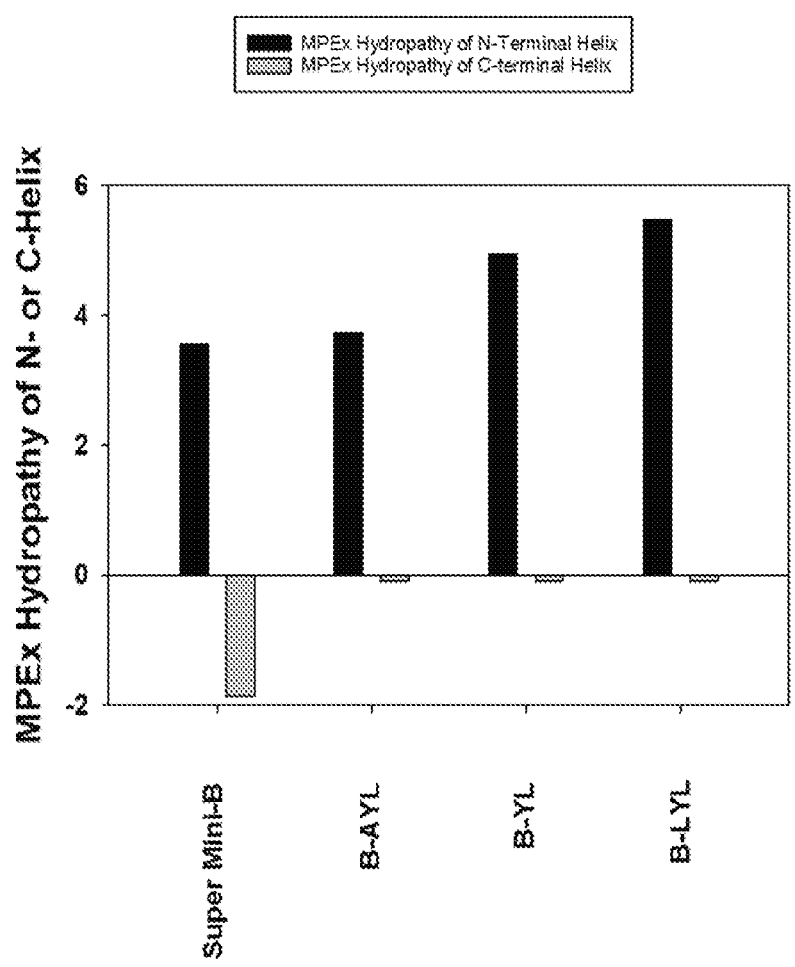
FIG. 4 shows MPEx hydropathies for the N-terminal (in black) and C-terminal (in gray) α-Helices of B-YL peptides. Named sequences are Super Mini-B, B-AYL, B-YL, and B-LYL. Hydropathy (kcal/mol) is a measure of the hydrophobic partitioning for helical peptides into membrane environments, determined using MPEx (Membrane Protein Explorer). Positive hydropathy predicts elevated lipid binding for helical peptides, while more negative values forecast greater water solubility.

FIG. 4 shows the MPEx hydropathies for the N- and C-terminal α-Helices of B-YL peptides. Named sequences are Super Mini-B, B-AYL, B-YL and B-LYL. Hydropathy (kcal/mol) is a measure of the hydrophobic partitioning for helical peptides into membrane environments, determined using MPEx (Membrane Protein Explorer). Positive hydropathy predicts elevated lipid binding for helical peptides, while more negative values forecast greater water solubility.

For MPEx analysis of Super Mini-B, FIG. 4 indicates that the N-terminal α-helix has a positive hydropathy of 3.55 kcal/mol, while the corresponding value for the C-terminal α-helix is −1.87. These MPEx results predict that the more hydrophobic N-terminal α-helix will insert deeper in membrane bilayers than will the C-terminal helix. Subsequent physical experiments and theoretical Molecular Dynamics (MD) simulation confirm this prediction, and suggest that the elevated surfactant activity observed for Super Mini-B is at least partially due to enhanced membrane binding.

Similar MPEx calculations for B-YL, B-AYL and B-LYL indicated higher membrane affinities than that of Super Mini-B. Specifically, FIG. 4 shows that the hydropathy of the N-terminal helix ascends in the following order: Super Mini-B <B-AYL<<B-YL<B-LYL, while the corresponding hydropathy of the C-terminal helix ascends in the following order: Super Mini-B<<B-AYL B-YL B-LYL. These findings raise the possibility that the named BYL peptides may exhibit high in vitro surfactant activities (FIGS. 1 and 2) due to elevated membrane affinity, which compensates for the absence of disulfide bridges.

Example 3

Preclinical and Clinical Testing

Earlier examples have shown that it is possible to improve oxygenation and lung function in spontaneously breathing rabbits with acute lung injury, supported with noninvasive ventilation (nasal CPAP), by administering aerosolized synthetic surfactant (Walther et al. in PeerJ, 403; 2014). This example further optimizes aerosol delivery of synthetic surfactant and adapts this technique so it can ultimately be used in premature infants in the developing world with breathing problems (respiratory distress syndrome, RDS) due to lung immaturity.

This example describes a pre-clinical development of aerosol delivery of synthetic surfactant to benefit premature infants with breathing problems who are supported with noninvasive ventilation (CPAP). This example will collect data on synthetic surfactant aerosol characteristics and output from various types of nebulizers and feasibility, dosing levels, lung delivery, and safety of synthetic surfactant aerosol delivery. With these data it will be feasible to move aerosol delivery of synthetic surfactant into the clinical realm and start saving the lives of premature infants with breathing problems who insufficiently respond to noninvasive ventilation where conventional mechanical ventilation is not an option.

This study design is unique because it paves the way for a new clinical approach for premature infants with breathing problems that cannot be sufficiently treated with noninvasive ventilation alone (i.e. nasal CPAP by nasal prongs or mask). This approach is especially important in environments with limited resources where intubation and mechanical ventilation are not generally available due to budget restraints and/or lack of medical and nursing skills. Next to the unconventional idea of surfactant aerosol delivery instead of administration via an endotracheal tube, this application is unique because it uses synthetic surfactant that has been designed to optimally associate with phospholipids and has a far lower price tag (less than twenty dollars per standard dose) than current clinical surfactant preparations. The proposed experiments will deliver the preclinical data necessary to bring aerosolized synthetic surfactant to clinical fruition.

This example will test dry instead of wet synthetic surfactant for aerosolization, because dry surfactant has a longer shelf life and does not require refrigeration. The previous examples indicate that lung delivery of synthetic surfactant aerosol should be increased to optimize its effects on lung function. Higher aerosol delivery to the lungs can theoretically be achieved by using higher doses, a higher dose rate (mg/min), a longer delivery time and/or adaptation of the delivery technique (e.g. via a face mask as a spacer or by using nasopharyngeal instead of nasal prongs to reduce nasal losses). The efficacy of these changes should be confirmed in vitro by measuring aerosol characteristics (particle size distribution, surface activity) and in vivo by establishing their effects on lung function and spreading of surfactant throughout the lungs in surfactant-deficient animals. The lack of toxicity for synthetic surfactant aerosol will be demonstrated with non-acute animal experiments.

This example has the following objectives. Objective (1): Compare dry and wet synthetic surfactant preparations by measuring particle size (Mass Median Aerodynamic Diameter, MMAD) distribution of their aerosols (generated with a dry powder, cq a vibrating membrane nebulizer) using laser diffraction particle sizing as they are blown from the tip of the nasopharyngeal prongs or nasal masks and checking their surfactant output, chemical composition (integrity, concentration) by mass spectroscopy and surface activity by captive bubble surfactometry. Synthetic surfactant will be produced as described in the previous examples. This example will use a dry powder nebulizer. This example will vary, adapt or redesign the peptide and/or phospholipids composition of the synthetic surfactant, if necessary, to guarantee surfactant aerosol particle sizes (MMAD) in the 1-4 µm range and a minimum surface tension <2 nM/M. Likewise this example can make changes in the design of the nebulizers to quality control and optimize their output.

Objective (2): Optimize synthetic surfactant dose delivery to the lungs during nasal CPAP with nasal/nasopharyngeal prongs or a nasal mask. Using the data obtained in the previous examples, dose-response curves will be made by varying the dose, dose rate and/or duration of surfactant delivery with a preference for short delivery periods or multiple doses as these are more practical in resource poor circumstances. Nasal masks are relatively easy to use but permit nasal passage that may lead to a considerable loss of aerosolized surfactant and need to be taken into account when optimizing dose delivery. These tests will use a premature infant nose throat-model (like the PrINT-model) and need to be followed by confirmation in animal models of surfactant deficiency (objective 3).

Objective (3): Based on the findings in objectives 1 and 2, the efficacy of a synthetic surfactant aerosol application will be assessed in 2 animal models: (a) the young adult rabbit with acute lung injury induced by repetitive saline lung lavages and mechanical ventilation, and (b) the CPAP-stable, non-intubated, spontaneously breathing premature lamb with surfactant deficiency due to lung immaturity. The rabbit model of acute lung injury will be used to screen out the best advanced synthetic surfactant aerosol to be tested in premature lambs supported with nasal CPAP. The premature lamb is an excellent model for surfactant deficiency because it mimics the clinical condition of premature infants with RDS and can be supported for longer periods of time to test for lack of synthetic surfactant toxicity. Lung function will be determined by measuring oxygenation, lung volume and lung compliance, whereas surfactant spreading throughout the lungs will be determined with in vivo quantitative bioluminescent imaging. Analysis of bronchoalveolar lavage fluid and histology will provide information on intrapulmonary effects (including toxicity) of synthetic surfactant. To demonstrate lack of toxicity of synthetic surfactant, a subgroup of premature lambs will be supported for a 48 hour period.

Objective (4): Development of a protocol for clinical studies testing synthetic surfactant aerosol delivery in spontaneously breathing premature infants supported on nasal CPAP for RDS. The protocol will describe optimal synthetic surfactant composition for aerosolization and technical points on use of nebulizer and nasal CPAP (bubble CPAP) during and after completion of synthetic surfactant aerosol delivery. This protocol will rely on the various experiments described in objectives 1-3.

Optimizing aerosolization. Synthetic surfactant to be tested includes single peptide (only a SP-B or a SP-C mimic) and multiple peptide (a SP-B and a SP-C peptide) preparations at various concentrations (1-3%) in standard phospholipid mixtures such as DPPC:POPC:POPG 5:3:2 or DPPC:POPG 7:3. Particle size (MMAD) distribution of synthetic surfactant aerosols generated with a dry powder inhaler and a vibrating membrane nebulizer will be measured using diffraction spectrometry. Integrity of the chemical composition of the aerosols will be measured by mass spectroscopy. Delivery efficacy will be determined by weighing wet aerosol samples. Surface activity of the synthetic surfactant aerosols will be measured with captive bubble surfactometry. The required characteristics of synthetic aerosols include a MMAD in the 1-4 µm range and minimum surface tension <2 nM/M. The goal of these experiments is to determine the optimal composition of a synthetic surfactant that can be aerosolized without loss of integrity and activity. SP-B and SP-C peptides will be produced by chemical synthesis and phospholipids will be bought or (in case of phosphonolipids synthesized) on an as needed basis.

Optimizing surfactant delivery in vitro. Using a premature infant nose throat (upper airway) model this example will produce dose-response curves by varying the nasal device (nasal/nasopharyngeal prongs, nasal/face mask), CPAP settings (flow, PEEP), dose rate and/or duration of surfactant delivery and measuring its impact on emitted (total amount of surfactant emitted by the nebulizer) and lung dose (amount of surfactant recovered in the impactor). Though aerosol drug delivery is considerably less than intratracheal bolus instillation, the objective is to deliver at least 25% of current clinical surfactant dosages to the lung.

In vivo studies. Studies in CPAP-supported, spontaneously breathing lavaged rabbits and premature lambs will provide data on lung function (oxygenation, compliance) and, at the end of the experiment, on surfactant delivery and spreading throughout the lungs with in vivo quantitative bioluminescent imaging. Lavage fluid is used for measures of alveolar protein leakage, indicators of inflammation and parameters of surfactant metabolism and lung tissue is collected for histology. Young adult rabbits (body weight 1.0-1.3 kg) receive anesthesia, followed by inserting of a venous line via a marginal ear vein and surgical placement of a carotid arterial line to monitor heart rate and blood pressure. Rabbits are intubated orally and stabilized on a Sechrist ventilator. Airway flow and pressures and tidal volume are monitored continuously with a pneumotachograph connected to the tracheal tube and a pneumotach system. If the $PaO_2$ is >500 torr at a peak inspiratory pressure <15 cm H2O, the rabbit undergoes repeated standardized saline lung lavages until PaO2 values <150 torr are reached. At this point half of the rabbits are assigned to continue mechanical ventilation (Intermittent Positive Pressure Ventilation, IPPV) while paralyzed and the other half are weaned to nasal CPAP after spontaneous breathing is established. The nebulizer is inserted into the system under the "Y" connector and the rabbits receive the experimental synthetic surfactant aerosol. After completion of the aerosol delivery, arterial pH and blood gases are repeated at 15 min intervals until the animals are sacrificed 2 hours thereafter. After completion of a postmortem pressure-volume curve with an open chest, the lungs are removed, weighed, surfactant spreading in the lungs is determined with bioluminescent imaging using an IVIS Lumina II system (and synthetic surfactant labeled with an inert bioluminescent probe), and the lungs will undergo a standard saline bronchoalveolar lavage (BAL). BAL fluid is used for measures of alveolar leakage (albumin, fibrin), indicators of inflammation (cell counts, myeloperoxidase activity, pro-inflammatory chemokines/cytokines) and parameters of surfactant metabolism (sustained efficacy, toxicity, recovery of endogenous surfactant secretion) and the right upper lung lobe is perfusion-fixed in situ for histological analysis.

Premature lambs are born by cesarean section at 135-137 days (term is ~145 days) of gestation after pretreatment of the ewe with bethamethasone 24 and 48 h prior to delivery to advance fetal lung maturation. Directly after birth the lamb is placed on heated and humidified nasal CPAP (bubble CPAP with PEEP 5-10 cm H2O, and 100% oxygen) using binasal prongs or a custom-made nasal mask. Catheters are placed in an umbilical artery and an umbilical vein. Airway flow and pressures and tidal volume are monitored continuously with a pneumotachometer system. Aerosolized synthetic surfactant will be given after establishment of respiratory failure as defined by elevated $PaCO_2$ levels and low pH values on at least two blood gas samples at or before 1 h of age. The arterial line is used for blood gas sampling (every 15 min) and monitoring of blood pressure and heart rate, the venous line for maintenance fluids. Maternal blood is drawn in heparinized syringes to transfuse the lambs in case of hypotension or blood loss. Lambs are euthanized 4 hours (acute experiments) or 48 hours (chronic experiments including safety testing) after aerosol delivery of synthetic surfactant. The post-mortem sequence of data collection is identical to that used in the rabbit experiments described above. The experimental surfactant which came out on top in the rabbit experiments will be tested in 8 preterm lambs and compared to 8 control lambs, which will receive a bolus surfactant of comparable composition using the minimally invasive surfactant treatment (MIST) approach [9]. In MIST a narrow-bore catheter is inserted under direct vision through the vocal cords of a premature infant supported with nasal CPAP. This example will use up to 20 ewes with singleton pregnancies (including experimental losses) in the second year of the project.

Development of a protocol for clinical studies testing synthetic surfactant. Aerosol delivery in spontaneously breathing premature infants supported on nasal CPAP for RDS. The protocol will describe optimal synthetic surfactant composition for aerosolization and technical points on use of nebulizer and nasal CPAP (bubble CPAP) during and after completion of synthetic surfactant aerosol delivery. This protocol will rely on the various experiments described in objectives 1-3.

The invention claimed is:

1. An isolated peptide comprising:
   (i) a first fragment comprising the amino acid sequence of XWLXRALIKRIQAZI (SEQ ID NO: 1) and
   (ii) a second fragment comprising the amino acid sequence of RZLPQLVXRLVLRXS (SEQ ID NO: 2), wherein:
   (a) X is any amino acid but at least one amino acid at the X positions is Y or F, and
   (b) Z is any amino acid but at least one amino acid at the Z positions is not methionine.

2. The peptide of claim 1, further comprising (iii) a turn between the first fragment and the second fragment.

3. The peptide of claim 2, wherein the turn comprises PKGG (SEQ ID NO: 3).

4. The peptide of claim 2, wherein the turn can form a salt bridge between amino acids within the turn or between the turn and the first or second fragment.

5. The peptide of claim 2, wherein the turn comprises DATK (SEQ ID NO: 4).

6. The peptide of claim 1, wherein the first fragment is at the N-terminal end of the second fragment, and wherein the peptide further comprises an insertion sequence at the N-terminal end of the first fragment.

7. The peptide of claim 6, wherein the insertion sequence comprises FPIPLPY (SEQ ID NO: 5).

8. The peptide of claim 1, wherein the peptide is 100 amino acids in length or shorter.

9. The peptide of claim 1, wherein each amino acid at the X positions is not cysteine.

10. The peptide of claim 9, wherein at least one amino acid at the X positions is Y.

11. The peptide of claim 1, wherein each amino acid at the Z position is not methionine.

12. The peptide of claim 1, wherein the first fragment comprises the amino acid sequence selected from the group consisting of SEQ ID NO: 11-18.

13. The peptide of claim 1, wherein the second fragment the amino acid sequence selected from the group consisting of SEQ ID NO: 19-26.

14. The peptide of claim 1, comprising the amino acid sequence selected from the group consisting of SEQ ID NO: 27-58.

15. A composition comprising a peptide of claim 1 and one or more phospholipid.

16. The composition of claim 15, wherein the one or more phospholipid is selected from the group consisting of dipalmitoylphosphatidylcholine (DPPC), palmitoyloleoyl-phosphatidylcholine (POPC), phosphatidylglycerol (PG), palmitoyloleoylphosphatidylglycerol (POPG), cholesterol (Chol), 1,2-Dioleoyl-sn-glycero-3-phosphocholine (DOPC), 1-Palmitoyl-2-oleoyl-sn-glycero-3-phosphoethanolamine (POPE), 1-palmitoyl-2-oleoylsn-glycero phosphocholine (POPS), 1,2-Distearoyl-sn-glycero-3-phosphocholine (DSPC), 1,2-Dipalmitoyl-sn-glycero-3-phosphoethanolamine (DPPE), 1,2-dipalmitoyl-sn-glycero-3-phosphoglycerol (DPPG), DEPN-8, PG-1 and combinations thereof.

17. The composition of claim 16, wherein the one or more phospholipid comprises DPPC, POPC and POPG.

18. The composition of claim 17, wherein the DPPC, POPC and POPG are at ratio of about (4-6):(2-4):(1-3).

19. A method of treating surfactant deficiency or dysfunction in a patient in need thereof, comprising administration to the patient a composition of claim 15.

20. The method of claim 19, wherein the surfactant deficiency or dysfunction comprises a respiratory distress syndrome in an infant or a respiratory distress syndrome secondary to surfactant deficiency or lung immaturity in a premature or near-term infant.

* * * * *